(12) United States Patent
Onishi

(10) Patent No.: US 11,786,624 B2
(45) Date of Patent: Oct. 17, 2023

(54) AROMA COMPONENT VOLATILIZATION DEVICE, AND METHOD FOR MANUFACTURING AROMA COMPONENT VOLATILIZATION DEVICE

(71) Applicant: BELL CODE CO., LTD., Miyazaki (JP)

(72) Inventor: Masaya Onishi, Miyazaki (JP)

(73) Assignee: BELL CODE CO., LTD., Miyazaki (JP)

( * ) Notice: Subject to any disclaimer, the term of this patent is extended or adjusted under 35 U.S.C. 154(b) by 0 days.

(21) Appl. No.: 18/010,786

(22) PCT Filed: Dec. 20, 2021

(86) PCT No.: PCT/JP2021/020517
§ 371 (c)(1),
(2) Date: Dec. 15, 2022

(87) PCT Pub. No.: WO2022/070506
PCT Pub. Date: Apr. 7, 2022

(65) Prior Publication Data
US 2023/0201402 A1    Jun. 29, 2023

(30) Foreign Application Priority Data
Oct. 2, 2020  (JP) ................. 2020-167646

(51) Int. Cl.
*A61L 9/03* (2006.01)
*B32B 38/04* (2006.01)

(52) U.S. Cl.
CPC ............... *A61L 9/03* (2013.01); *B32B 38/04* (2013.01); *A61L 2209/135* (2013.01); *B32B 2038/047* (2013.01); *B32B 2307/302* (2013.01)

(58) Field of Classification Search
CPC ..... A61L 9/03; A61L 2209/135; B32B 38/04; B32B 2038/047; B32B 2307/302
See application file for complete search history.

(56) References Cited

U.S. PATENT DOCUMENTS

2015/0086752 A1* 3/2015 Rasmussen ......... B32B 37/0076
428/167

FOREIGN PATENT DOCUMENTS

| JP | 58-105337 U1 | 7/1983 |
| JP | S 58-105337 U | 7/1983 |
| JP | 58-145848 A | 8/1983 |
| JP | 2-51534 U1 | 4/1990 |
| JP | H 2-51534 U | 4/1990 |
| JP | 2003-220088 A | 8/2003 |
| JP | 3125679 U | 9/2006 |
| JP | 2010-022405 A | 2/2010 |

(Continued)

*Primary Examiner* — Sean E Conley
*Assistant Examiner* — Brendan A Hensel
(74) *Attorney, Agent, or Firm* — Heedong Chae; Lucem, PC

(57) ABSTRACT

The aroma component volatilization device includes a bag containing a heating element that generates heat when exposed to air. At least one surface of the bag is composed of a thermally conductive sheet and a holding sheet. The thermally conductive sheet includes an aluminum layer containing aluminum on at least one entire surface of the sheet. An aroma component L is applied to the holding sheet. The thermally conductive sheet is disposed on the heating element side.

5 Claims, 11 Drawing Sheets

(56) References Cited

FOREIGN PATENT DOCUMENTS

| JP | 2016-78906 A | | 5/2016 | |
|----|--------------|---|--------|----------|
| JP | 2019/024924 | * | 2/2019 | ............... A61F 7/03 |
| JP | 2019-24924 A | | 2/2019 | |

* cited by examiner (a)

(b)

(c)

(a)

(b)

(c)

AROMA COMPONENT VOLATILIZATION DEVICE, AND METHOD FOR MANUFACTURING AROMA COMPONENT VOLATILIZATION DEVICE

TECHNICAL FIELD

The present invention relates to an aroma component volatilization device for accelerating the volatilization of a volatile aroma component with heat and a method for manufacturing such an aroma component volatilization device.

BACKGROUND ART

Aroma component volatilization devices used in cars, houses, etc., are composed of a bag containing a heating element that can cause a chemical reaction and generate reaction heat. The heating element heats an aroma component such as perfume or essential oil, which is disposed near the bag to accelerate the volatilization of the components, thereby diffusing aroma. Of these aroma component volatilization devices, those that include a heating element which causes an oxidation reaction do not need electricity, flame, water, etc. Thus, these devices are highly convenient because of their ease in handling and the wide range of places where they can be used. For example, one such aroma component volatilization device is shown in Patent Literature 1.

The aroma component volatilization device shown in Patent Literature 1 includes a bag composed of a single or laminated sheet containing a sealant material. The bag contains a powdery heating element that can cause an oxidation reaction and generate heat when exposed to air. One side of the bag is covered with a holding sheet containing an aroma component. As a result, when the heating element reacts with oxygen and generates heat, the aroma component contained in the holding sheet is heated and volatilized.

CITATION LIST

Patent Literature

Patent Literature 1: Japanese Unexamined Patent Application Publication No. 2010-22405 (Pages 3 and 4, FIG. 1)

SUMMARY OF INVENTION

Technical Problem

The aroma component volatilization device according to Patent Literature 1 can volatilize the volatile component through the bag when the aroma component is heated by the heating element for generating heat. However, if the heating element happens to slide over to one side in the bag, some areas of the bag that are located near the heating element may be heated exclusively and other areas may be left unheated. In such cases, the aroma component cannot continue to volatilize at a substantially constant amount for many hours.

The present invention has been made in view of the above problems, and it is an object of the present invention to provide an aroma component volatilization device that can volatilize an aroma component at a substantially constant amount for many hours, and a method for manufacturing such an aroma component volatilization device.

Solution to Problem

To achieve the above object, an aroma component volatilization device according to the present invention includes a bag having therein a heating element that generates heat when exposed to air, an inner layer of the bag being a thermally conductive sheet on a base of which a thermally conductive material is vapor-deposited, and an outer layer of the bag being a holding sheet having air permeability. According to this structure, even if the heating element slides over to one side in the bag, the generated heat can spread throughout the thermally conductive sheet, thereby heating the holding sheet uniformly. Thus, the aroma component can continue to volatilize at a substantially constant amount for many hours.

The thermally conductive sheet and the holding sheet may be spot bonded at intervals. According to this structure, the thermally conductive sheet and the holding sheet together form an air layer between them, and the air layer prevents the aroma component from being heated excessively.

The thermally conductive sheet may have aluminum that is vapor-deposited on the base that is made of resin in the form of a sheet. According to this structure, the flexible aluminum sheet preferably facilitates the storage and portability of the device.

The thermally conductive sheet may be bonded to the holding sheet at a part of the resin that melts and adheres to the holding sheet while the thermally conductive sheet is being perforated. According to this structure, excessive inhibition of heat transmission from the thermally conductive sheet to the holding sheet can be prevented.

To solve the aforementioned problems, a method according to the present invention for manufacturing an aroma component volatilization device includes the following steps. A thermally conductive sheet is laminated on a top surface of a holding sheet, the thermally conductive sheet being composed of a base made of resin and a thermally conductive material vapor-deposited on the base. At least one through-hole passing through from the thermally conductive sheet to the holding sheet is formed by using a perforating member heated hot enough to melt the base. A part of the base melted by the perforating member is caused to flow out and adhere to the holding sheet, thereby forming the thermally conductive sheet and the holding sheet into a single laminated sheet. The laminated sheet is folded along the approximate midline with the thermally conductive sheet inside. Peripheries of the folded laminated sheet are bonded.

According to this structure, even if the heating element slides over to one side in the bag, the generated heat can spread throughout the thermally conductive sheet, thereby heating the holding sheet uniformly. This facilitates the manufacture of the aroma component volatilization device that enables the aroma component to continue to volatilize at a substantially constant amount for many hours.

The step of forming the single laminated sheet may include forming the through-holes at fixed intervals, thereby forming an air layer partitioned into a plurality of air sections between adjacent ones of a plurality of through-holes. According to this structure, the air layer can be formed at regular intervals in the laminated sheet. This prevents the essential oil that drips onto the holding sheet from being heated excessively, thus keeping the effects of the aroma of the essential oil for many hours.

The method may further include a step of dripping essential oil as an aroma component onto the holding sheet. According to this structure, the aroma component of the essential oil dripped onto the holding sheet can be diffused over a wide area by a rising airflow.

DESCRIPTION OF EMBODIMENTS

The embodiments of the aroma component volatilization device according to the present invention will be described as follows by means of examples.

Example 1

An aroma component volatilization device according to a first exemplary embodiment will now be described with reference to FIGS. 1 to 6.

Figure 1:
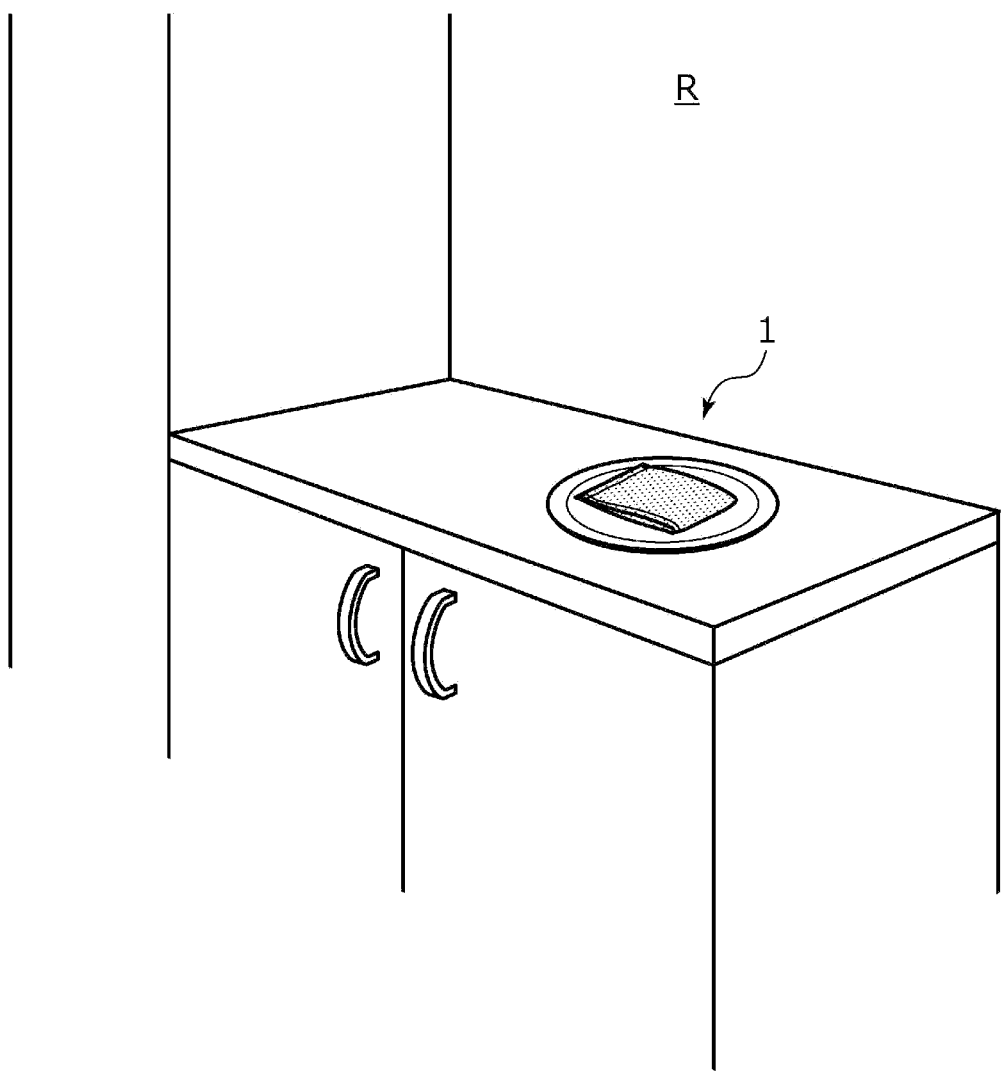
FIG. 1 is a perspective view of an aroma component volatilization body as an aroma component volatilization device according to a first embodiment of the present invention.

An aroma component volatilization body 1 as the aroma component volatilization device may be placed in an indoor space R such as an entrance as shown in FIG. 1 to volatilize an aroma component, for example, perfume or essential oil. Note that, in FIG. 1, the aroma component volatilization body 1 is used by placing it on a plate, but may alternatively be placed directly on a floor, or a surface such as a top panel of a shoe rack or table.

Figure 2:
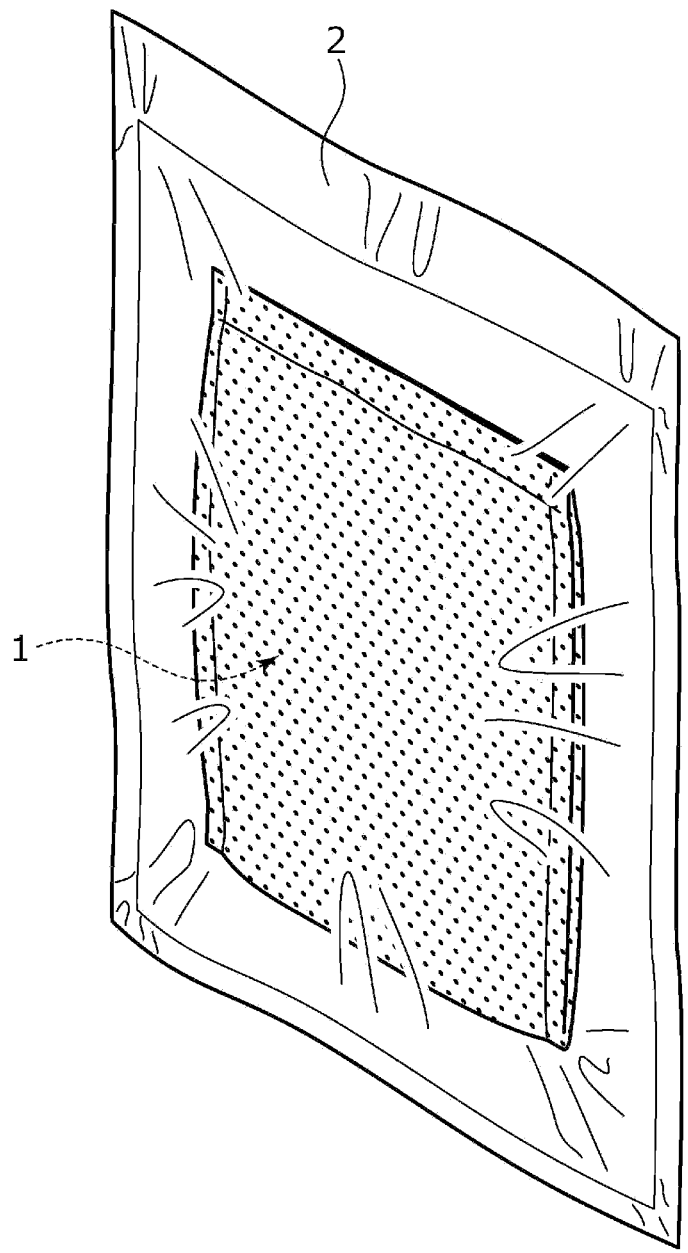
FIG. 2 is a perspective view of the aroma component volatilization body of the first embodiment when sealed in a package.

As shown in FIG. 2, the aroma component volatilization body 1 is vacuum-sealed in a package 2 when unused. The term "vacuum" as used herein includes not only a perfect vacuum but also a state where the aroma component volatilization body 1 is unlikely to be exposed to outside air.

Figure 3:
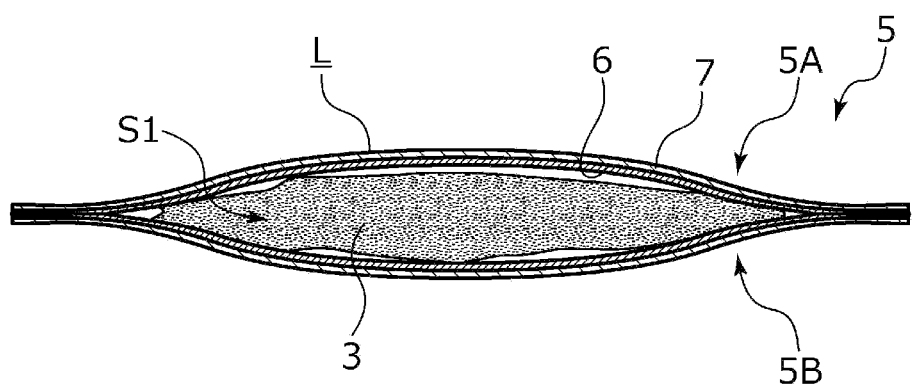
FIG. 3 is a sectional view of the aroma component volatilization body of the first embodiment.

As shown in FIG. 3, the aroma component volatilization body 1 is composed of a bag 5 and a heating element 3 contained in the bag 5. The heating element 3 is in a powder form, such as iron powder and generates heat when exposed to air. The material of the heating element 3 can be appropriately selected from, for example, iron powder, water, activated carbon, vermiculite, water-absorbent resin, and salts.

The bag 5 is composed of a thermally conductive sheet 6, which defines an accommodation space S1 where the heating element 3 is contained, and a holding sheet 7 covering the thermally conductive sheet 6. The bag 5 is flat in shape and includes a laminated sheet-like aroma surface 5A having the holding sheet 7 on which essential oil L as an aroma component may be dripped, and a laminated sheet-like placement surface 5B, which is disposed to face the aroma surface 5A and is directly placed on the plate. Note that FIGS. 3 to 6 exaggerate the thickness of the thermally conductive sheet 6 and the holding sheet 7.

Figure 4:
FIGS. 4A, 4B, and 4C are views depicting formation of the bag.
Figure 4:
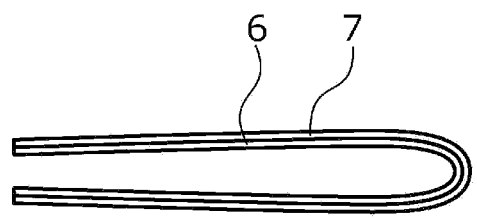
Figure 4:
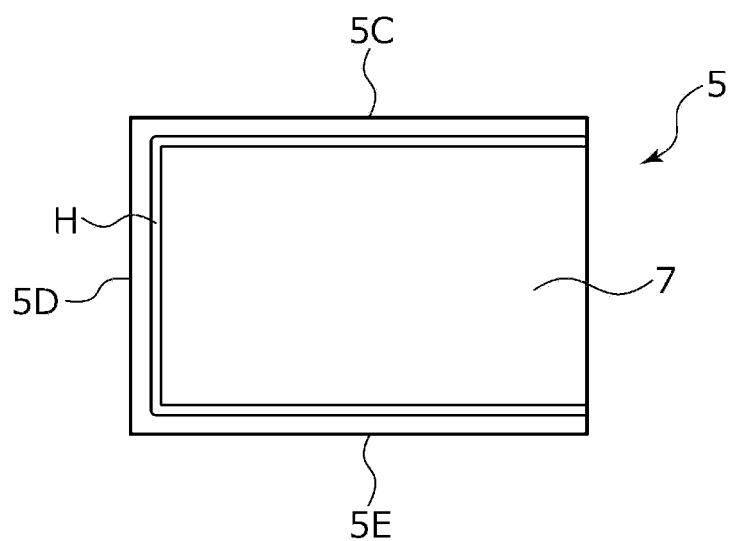

The manufacturing of the bag 5 and manufacturing processes will now be described with reference to FIGS. 4 to 6. Note that these processes do not include the description or illustration of the heating element 3. The bag 5 is formed such that the thermally conductive sheet 6 is laminated on and bonded to the holding sheet 7 (see FIG. 4A). Both sheets are rectangular when viewed from above. Next, the bonded sheets are folded with the thermally conductive sheet 6 inside (see FIG. 4B). Finally, three sides 5C, 5D, and 5E are each stacked and bonded by heat sealing H (see FIG. 4C). These processes enable the simple laminated formation of the aroma surface 5A and the placement surface 5B of the laminated sheet, each of which consists of the thermally conductive sheet 6 and the holding sheet 7.

Figure 5:
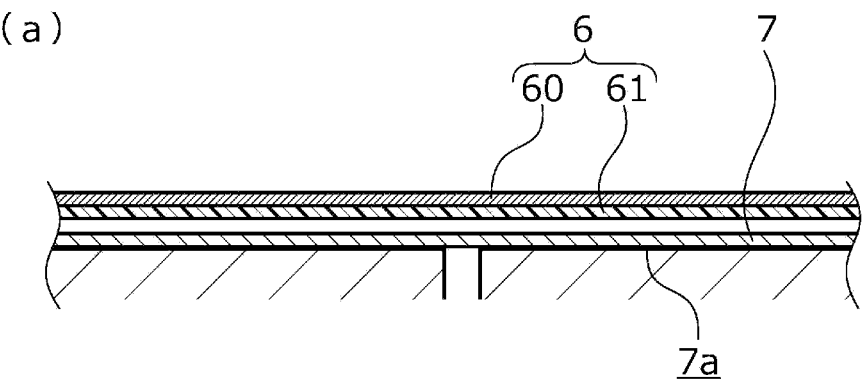
FIGS. 5A, 5B, and 5C are views depicting bonding of a thermally conductive sheet and a holding sheet.
Figure 5:
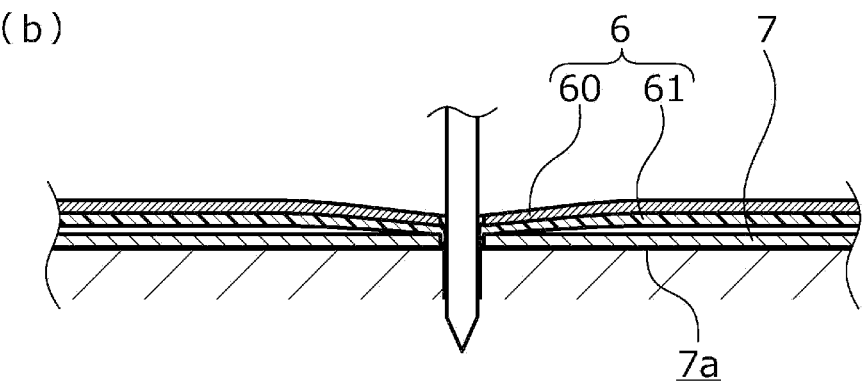
Figure 5:
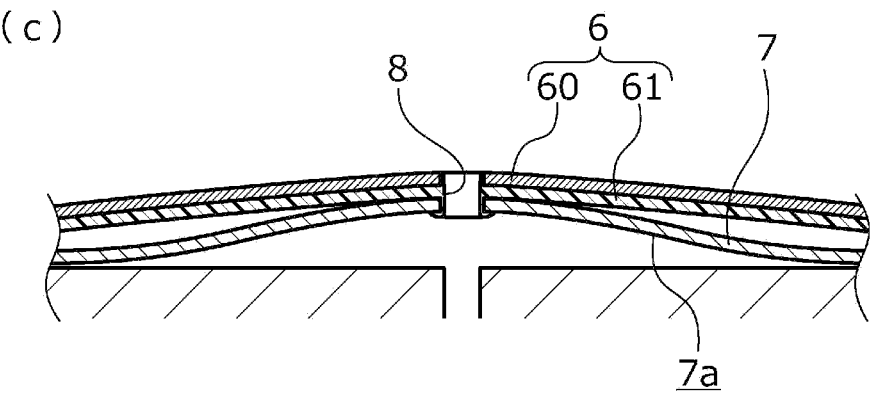

As shown in FIGS. 5A, 5B and 5C, the thermally conductive sheet 6 is composed of a sheet-like base 61 made of a highly flexible resin and an aluminum layer 60 formed by vapor-depositing aluminum on an entire surface of the base 61. The aluminum layer 60 may be composed of aluminum particles attached to the base 61 and allows the base 61 to be flexible. Thus, the thermally conductive sheet 6 has higher flexibility than aluminum foil formed by rolling aluminum. Note that FIGS. 5 and 6 exaggerate the sizes of the aluminum layer 60 and the base 61.

The holding sheet 7 is made of a material having air permeability such as nonwoven cloth. In the present example, the essential oil L is dripped onto the holding sheet 7 after the aroma component volatilization body 1 is taken out of the package 2. Alternatively, however, the essential oil L may be applied to holding sheet 7 while the aroma component volatilization body 1 is sealed into the package 2.

The thermally conductive sheet 6 and the holding sheet 7 are spot bonded at fixed intervals. Specifically, the spot bonding is performed such that the holding sheet 7 is placed on a workbench and the thermally conductive sheet 6 is laminated on the holding sheet 7 with the base 61 facing the holding sheet 7 (see FIG. 5A). Next, the laminated sheets are perforated from the aluminum layer 60 side to the holding sheet 7 side using a perforating member having a needle-like shape (see FIG. 5B).

The perforation operation is performed after the perforating member is heated enough to melt the perforated part of the resin of the base 61. The part of the base 61 or of the resin melted by the incoming perforating member is pushed out to an outer surface 7a of the holding sheet 7 (see FIG. 5B). After the heating of the perforating member is stopped and the molten part of the resin is cooled and hardened, the perforating member is pulled out of through-holes 8 (see FIG. 5C).

As a result, the molten part of the resin adheres to the outer surface 7a and is also entangled with fibers of the nonwoven cloth of the holding sheet 7. This achieves the bonding of the thermally conductive sheet 6 and the holding sheet 7. Note that the method of bonding the thermally conductive sheet 6 and the holding sheet 7 in the perforation operation may be appropriately changed. For example, when the tip of the perforating member reaches the holding sheet 7, the molten part of the resin may be flowed out to the holding sheet 7, and the aluminum layer 60 and the surface of the holding sheet 7 may be bonded by spot bonding. Alternatively, the aluminum layer 60 may be perforated using the perforating member to cause a part of the resin to flow out, so that the aluminum layer 60 attached to the flowed out part of the resin can come into contact with the holding sheet 7, thereby bonding the aluminum layer 60 and the surface of the holding sheet 7. Furthermore, instead of using the needle-like perforating member described so far, perforating energy can be sprayed to form the through-holes 8 in the aluminum layer 60.

The perforation operation provides the thermally conductive sheet 6 and the holding sheet 7 with the plurality of through-holes 8 having a diameter of about 75 μm at a density of $1,786,000/m^2$.

Figure 6:
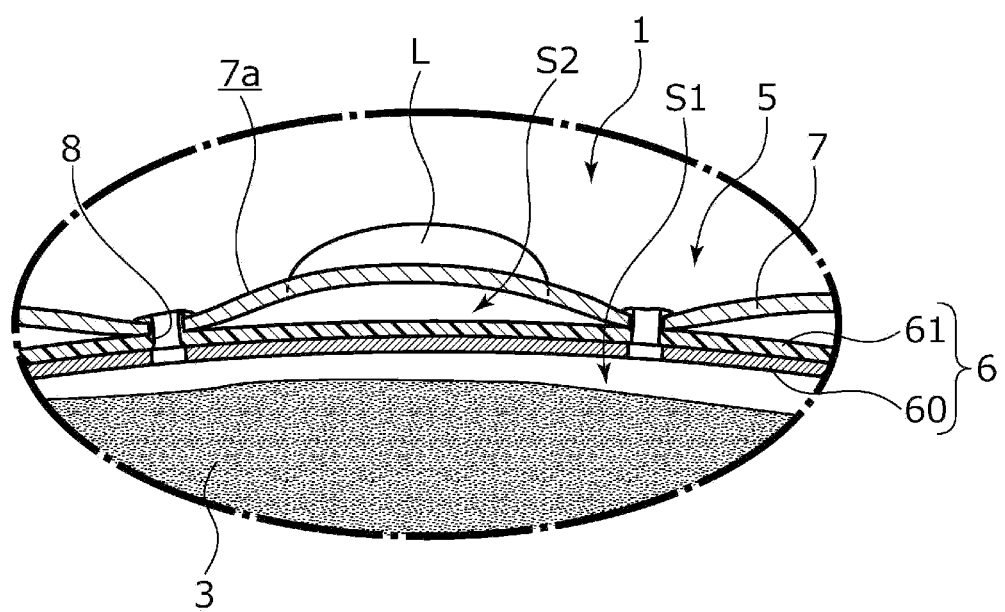
FIG. 6 is an enlarged sectional view of an essential part of the aroma component volatilization body.

As shown in FIG. 6, the through-holes 8 are formed with the thermally conductive sheet 6 pressed onto the holding sheet 7. Thus, those regions of the holding sheet 7 that are located around the through-holes 8 are compressed against the thermally conductive sheet 6. As a result, the regions of the holding sheet 7 that are more distant from the through-holes 8 are more warped and distant from the thermally conductive sheet 6. This warpage allows the formation of an air layer S2 between the thermally conductive sheet 6 and the holding sheet 7. Note that FIG. 6 exaggerates the size of a drip of the essential oil L.

As described above, according to the present example, as soon as the aroma component volatilization body 1 is taken out of the package 2, outside air flows into the accommodation space S1 through the plurality of through-holes 8 formed in the bag 5, and the heating element 3 reacts with oxygen and generates heat. Even if the heating element 3 slides over to one side in the bag 5, the generated heat can spread throughout the thermally conductive sheet 6, thereby heating the holding sheet 7 uniformly. Thus, the essential oil L can continue to volatilize at a substantially constant rate for many hours.

In particular, fluid aroma components such as the essential oil L may be in different positions within the bag 5 depending on, for example, the tilt angle at which the aroma component volatilization body 1 is placed or the position, on which such a fluid aroma component is dripped. However, according to this embodiment, the holding sheet 7 can be beneficially heated uniformly in the aroma component volatilization body 1.

In the aroma component volatilization body 1, the air layer S2 formed between the thermally conductive sheet 6 and the holding sheet 7 may prevent the essential oil L from being heated excessively. This prevents aroma alteration due to excessive heating.

In addition, the holding sheet 7 made of nonwoven cloth is high in air permeability, thus facilitating the supply of fresh air into the air layer S2 even after the air inside the layer S2 is heated and moved upward. This also facilitates the generation of a rising airflow, and accordingly, the volatilized essential oil L is easily diffused over a wide area by the rising airflow.

It is also preferable that the flexible thermally conductive sheet 6 is unlikely to be broken by a force in the bending or tensile direction during storage or transfer.

The highly hydrophobic base 61 of the thermally conductive sheet 6 can prevent the heating element 3 from getting wet due to the penetration of the essential oil L dripped onto the holding sheet 7. This prevents aroma alteration and insufficient heating of the heating element 3 caused when the essential oil L is directly heated by the heating element 3.

The thermally conductive sheet 6 and the holding sheet 7 are bonded together by the part of the resin melted in the perforation operation. As a result, unlike the case of bonding the thermally conductive sheet 6 and the holding sheet 7 at their opposing surfaces using an adhesive, the excessive inhibition of heat transmission from the thermally conductive sheet 6 to the holding sheet 7 can be prevented, and it prevents the aroma from being mixed with the odor of the adhesive when the essential oil L is heated.

In the aroma component volatilization body 1, even if the essential oil L flows along the holding sheet 7, the flowing of the essential oil L into the accommodation space S1 through the through-holes 8 can be prevented by the small diameter of the through-holes 8 and the surface tension of the essential oil L.

Both the aroma surface 5A and the placement surface 5B of the bag 5 are composed of the thermally conductive sheet 6 and the holding sheet 7. Therefore, the placement surface 5B can be used for the volatilization of the essential oil L in the same manner as the aroma surface 5A, thus facilitating the application of the essential oil L.

As mentioned above, the aroma surface 5A and the placement surface 5B of the bag 5 are both composed of the thermally conductive sheet 6 and the holding sheet 7. Even when the bag 5 is placed on a plate, the aforementioned holding sheet 7 high in air permeability ensures air flowing through the downside through-holes 8 onto which the essential oil L is not dripped. Thus, the heating of the heating element 3 can be more stable than in the case of placing the thermally conductive sheet 6 directly on the plate.

Oxygen is more easily supplied to those parts of the heating element 3 that are closer to the placement surface 5B and promotes an oxidation reaction. The heat generated near the placement surface 5B is quickly transmitted from the aluminum layer 60 on the placement surface 5B side to the aluminum layer 60 on the aroma surface 5A side. This ensures the uniform and rapid heating of the entire holding sheet 7.

The aluminum layer 60 of the thermally conductive sheet 6 defines the accommodation space S1, which is likely to come into contact with the heating element 3. Thus, as compared with the case where the base 61 defines the accommodation space S1, the holding sheet 7 can be heated faster and more uniformly. Furthermore, the part of the resin melted in the perforation operation easily reaches the outer surface 7a of the holding sheet 7, improving the bonding efficiency of the thermally conductive sheet 6 and the holding sheet 7.

The aroma surface 5A and the placement surface 5B of the bag 5 are both provided with the plurality of through-holes 8. Therefore, the air flowed into the accommodation space S1 through the downside through-holes 8 is heated by the heating element 3 and then flows out through the through-holes 8 of the aroma surface 5A. This facilitates the generation of a rising airflow, allowing the volatilized essential oil L to be diffused over a wide area by the rising airflow.

An experiment was conducted to analyze the temperature change of the holding sheet 7 of the aroma component volatilization body 1 over time. In this experiment, the aroma component volatilization body 1 had a size of 40 mm×40 mm and contained 4 mg of the heating element 3.

The through-holes 8 with a diameter of about 75 μm were formed at a density of 1,786,000/m² at fixed intervals. The time measurement was started when the package 2 was opened, and the temperature of the holding sheet 7 was measured about every minute. The temperature of the room used in the experiment was about 20 degrees, and the aroma component volatilization body 1 was placed on a plate without being shaken or rubbed, etc., to accelerate the oxidation reaction of the heating element 3.

It has been found through the experiment that the holding sheet 7 can reach 40 degrees in about 8 minutes, and be maintained at not less than 40 degrees for over four hours. The maximum temperature during the four hours was 50.3 degrees. The following facts are known from previous experiments. The temperature range of about 40 to 50 degrees is optimum to volatilize the essential oil L because of the best balance between the amount to be volatilized per unit time and the change in aroma due to heating (the balance between the concentration of aroma and the fragrance). At temperatures lower than this range, the aroma lacks both concentration and fragrance, whereas at temperatures higher than this range, the aroma is too strong and the fragrance quality is insufficient.

The diameter and the number per unit area of the through-holes may be appropriately changed as long as the temperature range of about 40 to 50 degrees can be maintained. It is preferable, however, that the through-holes be formed at a density of about 101,000,000/m² (with a diameter of 10 μm) to at a density of about 1,200,000/m² (with a diameter of 120 μm). This range is preferred in order to have a long enough time to ensure the above-mentioned temperature range and also in order to prevent both the flowing out of the heating element 3 and the leakage of the essential oil L into the accommodation space S1. Note that the diameter and number of the through-holes can be appropriately changed for some types of products that require higher temperature ranges.

Based on sensory test experiments conducted on 30 people to examine the correspondence between the size of a room and the time for the essential oil L to continue volatilizing, when the essential oil L was volatilized continuously for four hours in a room of about 30 m², 21 of the 30 people were generally satisfied.

These results indicate that a wide spectrum of users can enjoy the device provided that the temperature range of about 40 to 50 degrees can be kept for over four hours by adjusting the amount of the essential oil L to be dripped in accordance with the size of the room or the users' preference in aroma concentration.

Example 2

An aroma component volatilization device according to a second exemplary embodiment will now be described with reference to FIGS. 7 to 11. Note that components identical to those in the aforementioned example will be omitted.

Figure 7:
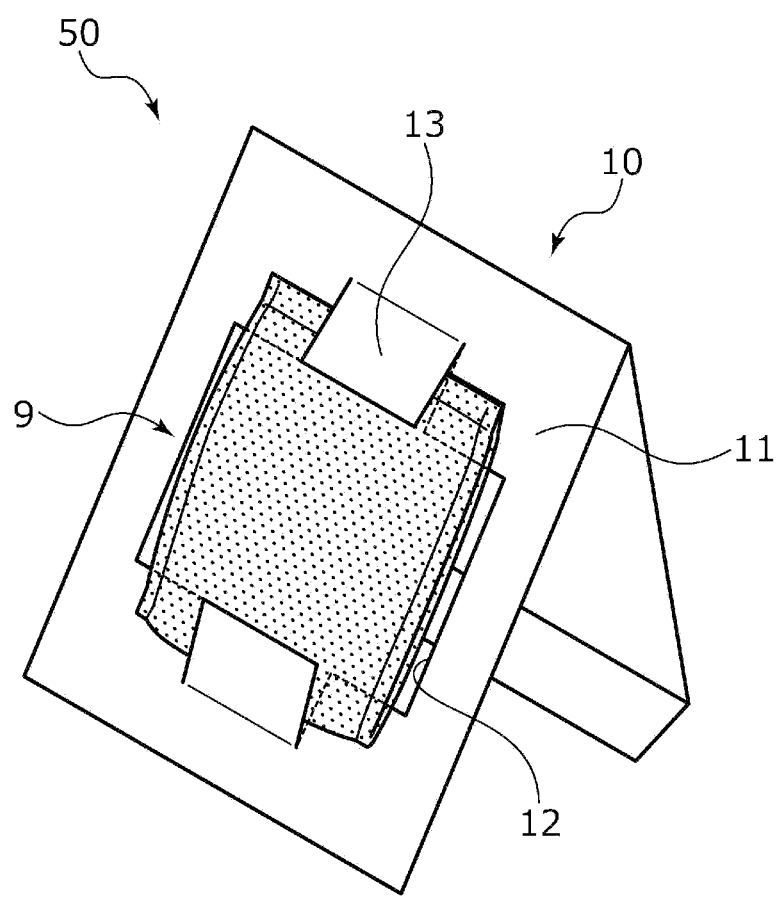
FIG. 7 is a perspective view of an aroma component volatilization device according to a second embodiment of the present invention.

As shown in FIG. 7, an aroma component volatilization device 50 includes an aroma component volatilization body 9, which is the same as the one in Example 1, and a support body 10, which can stand on a surface such as a plate and a top panel. The support body 10 can be, for example, a thin plastic plate or a cardboard and be folded into an inverted V shape. The support body 10 includes a flat placement portion 11 on which the aroma component volatilization body 9 is placed, an opening 12 communicated in the thickness direction of the placement portion 11, and a pair of upper and lower engagement pieces 13 for holding the aroma component volatilization body 9. While the aroma component volatilization body 9 is placed on the placement portion 11, the opening 12 ensures air permeability of the placement surface 5B (see FIG. 3). Consequently, the heating element 3 can be heated more appropriately than in the case of placing the aroma component volatilization body 9 directly on a surface.

Since the support body 10 is foldable, when not in use, the device 50 can be vacuum-sealed in the package 2 (see FIG. 2) with the aroma component volatilization body 9 held by the engagement pieces 13 and with the support body 10 folded. In this case, the aroma component volatilization device 50 can be stored compactly and be easily set up only by taking out the support body 10 from the package 2 and developing and standing the support body 10 on a surface.

The support body 10 can be easily formed as follows: bending a thin plastic plate, cardboard, etc.; cutting out the center part of the placement portion 11 to form the opening 12; and cutting and raising the parts of the placement portion 11 that are located above and below the opening 12 to form the engagement pieces 13.

Figure 8:
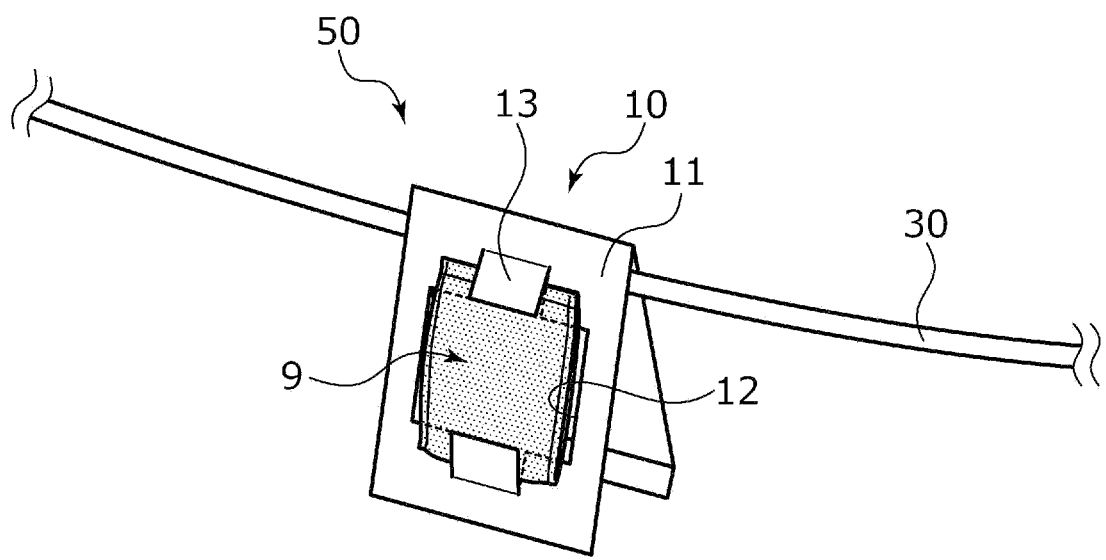
FIG. 8 is a perspective view of the aroma component volatilization device of the second embodiment when used in a different manner.
Figure 9:
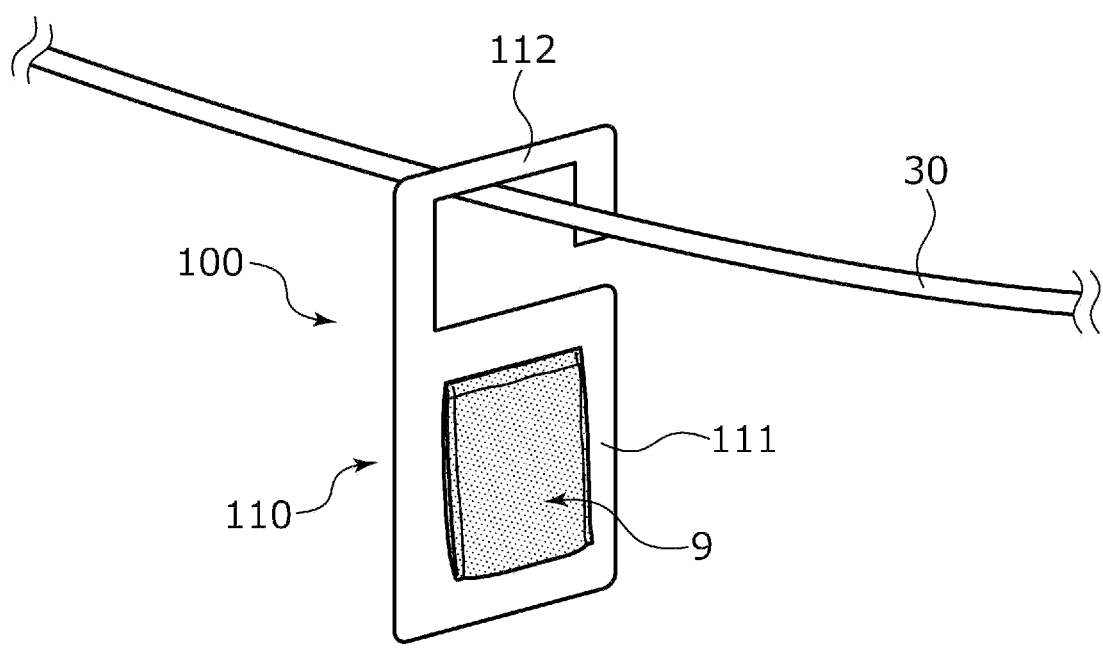
FIG. 9 is a perspective view of an aroma component volatilization device according to a modified version of the first embodiment.
Figure 10:
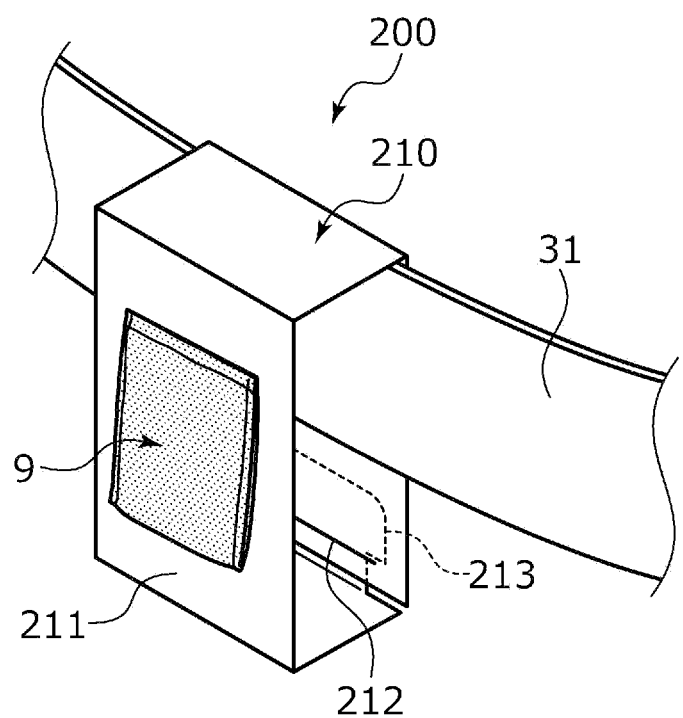
FIG. 10 is a perspective view of an aroma component volatilization device according to a modified version of the second embodiment.
Figure 11:
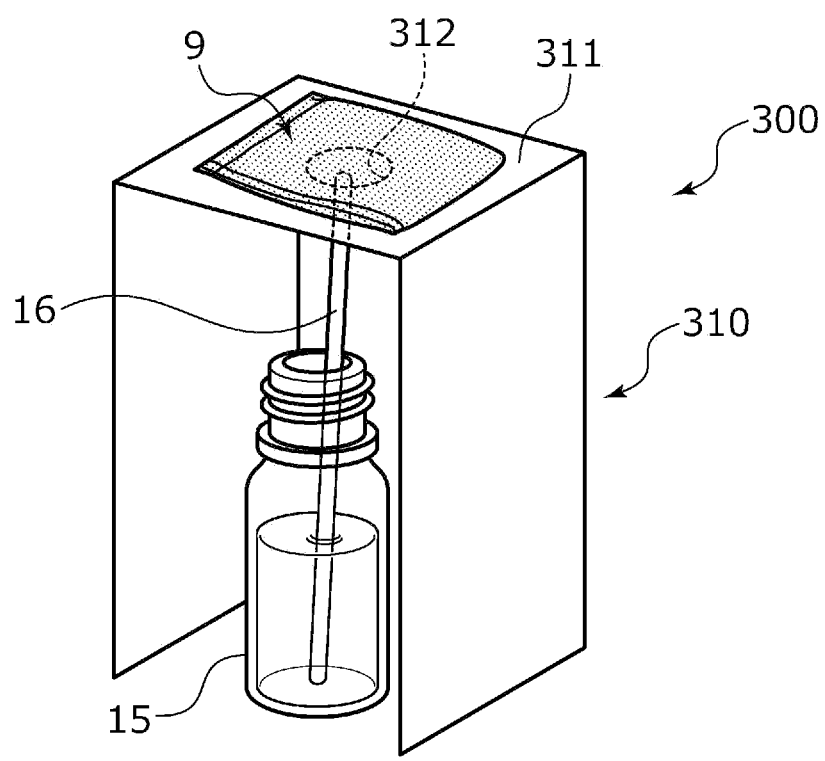
FIG. 11 is a perspective view of an aroma component volatilization device according to another embodiment.

The support body 10, which has an inverted V shape, can be hung on a hanging member 30 such as a string or wire as shown in FIG. 8.

A modified version of the above-described first embodiment of the aroma component volatilization device will be described as follows. An aroma component volatilization device 100 of the modified Example 1 includes a support body 110 having a placement portion 111 provided with an adhesive layer on which the placement surface 5B (see FIG. 3) of the aroma component volatilization body 9 is affixed. The support body 110 further has a hook 112, by which the device 100 is hung on the hanging member 30. Thus, even when the placement surface 5B is pasted on the placement portion 111, air permeability of the through-holes 8 can be ensured not only by the opening 12 (see FIGS. 7 and 8) but also by the holding sheet 7 and the air layer S2 which are included on the placement surface 5B (see FIG. 6). The adhesive layer may alternatively be formed on the placement surface 5B of the aroma component volatilization body 9. The methods of supporting the aroma component volatilization body 9 on the support body 110 is not limited to the use of an adhesive layer. The adhesive layer may be appropriately changed to, for example, an engagement piece, a double-sided adhesive tape, or a hook-and-loop fastener, etc.

A modified version of the above-described second embodiment of the aroma component volatilization device will be described as follows. An aroma component volatilization device 200 of the modified Example 2 includes a support body 210 having a placement portion 211 provided with an adhesive layer. The placement surface 5B (see FIG. 3) of the aroma component volatilization body 9 is affixed on the adhesive layer. The support body 210 further has a locking hole 212 at one end and an insertion piece 213 at the other end. The insertion piece 213 is inserted and fixedly secured into the locking hole 212, allowing the device 200 to be hung and attached to a belt 31. This structure enables users to walk around a room or go out with the aroma component volatilization body 9 on their bodies. Places to hang and attach the device 200 are not limited to the belt 31, and may be appropriately changed to other places such as a bag handle.

Another embodiment of the aroma component volatilization device 300 includes an inverted U-shaped support body 310 having a placement portion 311 provided with an adhesive layer. The placement surface 5B (see FIG. 3) of the aroma component volatilization body 9 is affixed on the adhesive layer. The support body 310 is set to straddle a bottle 15 containing the essential oil L. The bottle 15 has a bar-shaped member 16 made of filter paper in such a manner that the bottom end of the member 16 is put in the bottle 15 and the top end of the bar-shaped member 16 is in contact with the placement surface 5B through an opening 312 of the support body 310. Thus, the essential oil L in the bottle 15 can be constantly supplied to the aroma component volatilization body 9 through the bar-shaped member 16. As a result, the essential oil L can securely continue to volatilize for many hours.

Examples of the present invention have been thus described in detail. However, the scope of the present invention is not limited to the above examples; any modifications or additions can be made within the scope of the present invention.

For example, the bag has been described to have a flat shape including the aroma surface and the placement surface in the above-described examples. However, the shape of the bag can be appropriately changed to, for example, a polyhedron having four or more faces, such as a tetrahedron or a hexahedron, or can even be a cone or a column.

The aroma surface and the placement surface have been described to be sheet-like. However, the structure is not limited to this, and may alternatively be board-like or in other shapes as long as the bag can be formed.

The thermally conductive sheet has been described to be composed of a resin base in the form of a sheet, and aluminum vapor-deposited on an entire one-side surface of the base. However, the structure of the thermally conductive sheet is not limited to this. The base may be covered with aluminum foil or aluminum mesh, or any other thermally conductive materials may be appropriately used instead of aluminum.

Further alternatively, aluminum may be vapor-deposited on both sides of the base.

The thermally conductive sheet has been described to be disposed in such a manner that the base faces the holding sheet. However, the structure of the thermally conductive sheet is not limited to this. The sheet may alternatively be disposed in such a manner that the aluminum layer faces the holding sheet.

The thermally conductive sheet and the holding sheet have been described to be bonded together by perforation. However, the structure is not limited to this, and these sheets may be spot-bonded by heat sealing, adhesive, sewing, or other methods.

The thermally conductive sheet and the holding sheet have been described to compose all surfaces of the bag. However, the structure is not limited to this, and may alternatively compose at least one surface of the bag.

The holding sheet does not need to be made of nonwoven cloth, and the material is not particularly limited as long as it has certain air permeability and can hold a liquid or viscous body.

The aroma component has been described to be essential oil, but may alternatively be liquid perfume or other forms that are as fluid as liquid such as cream, gel, or powder. Further alternatively, the aroma component can be in the form of a capsule, a board, or others instead of fluid materials as long as it can be applied to the holding sheet.

The thermally conductive sheet and the holding sheet have been described to have a plurality of through-holes. However, the structure is not limited to this, and may alternatively have a single through-hole, for example, a long and narrow spiral through-hole.

REFERENCE SIGNS LIST

1 Aroma component volatilization body (aroma component volatilization device)
3 Heating element
5 Bag
5A Aroma surface
5B Placement surface
6 Thermally conductive sheet
7 Holding sheet
8 Through-hole
9 Aroma component volatilization body
10 Support body
11 Placement portion
12 Opening
13 Engagement piece
50 Aroma component volatilization device
60 Aluminum layer
61 Base
100, 200, 300 Aroma component volatilization device
110, 210, 310 Support body
111, 211, 311 Placement portion
312 Opening
L Essential oil (aroma component)
S1 Accommodation space
S2 Air layer

The invention claimed is:
1. An aroma component volatilization device comprising:
a bag including therein a heating element that generates heat when exposed to air and comprising:
an inner layer formed as a thermally conductive sheet comprising a base and a thermally conductive vapor-deposited material; and
an outer layer formed as a holding sheet having air permeability,
wherein the inner layer and the outer layer are spot bonded at fixed intervals to form an air layer between the thermally conductive sheet and the holding sheet, and
wherein a length of the inner layer between adjacent spot bonded locations, between which the air layer is formed, is different from a length of the outer layer between the adjacent spot bonded locations.
2. The aroma component volatilization device according to claim 1, wherein the thermally conductive vapor-deposited material is aluminum and the base comprises a resin sheet.
3. The aroma component volatilization device according to claim 1, wherein the thermally conductive sheet is bonded to the holding sheet at a part of the resin that melts and adheres to the holding sheet while the thermally conductive sheet is being perforated.
4. A method for manufacturing an aroma component volatilization device, comprising:
laminating a thermally conductive sheet on a top surface of a holding sheet, the thermally conductive sheet being composed of a base made of resin and a thermally conductive material vapor-deposited on the base, the holding sheet having air permeability;
forming at least one through-hole passing through from the thermally conductive sheet to the holding sheet by using a perforating member heated hot enough to melt the base;

spot bonding a part of the base melted in the step of forming the through-hole to the holding sheet, thereby forming a single laminated sheet composed of the thermally conductive sheet, the holding sheet, and an air layer formed therebetween;

folding the laminated sheet along an approximate midline with the thermally conductive sheet inside; and bonding peripheries of the folded laminated sheet, wherein a length of the inner layer between adjacent spot bonded locations, between which the air layer is formed, is different from a length of the outer layer between the adjacent spot bonded locations.

5. The method for manufacturing the aroma component volatilization device according to claim 4, further comprising:

dripping essential oil as an aroma component onto the holding sheet.

\* \* \* \* \*